(12) United States Patent
He et al.

(10) Patent No.: US 12,364,451 B2
(45) Date of Patent: Jul. 22, 2025

(54) STENOSIS ASSESSMENT METHOD AND DEVICE BASED ON INTRACRANIAL DSA IMAGING (71) Applicant: Hangzhou ArteryFlow Technology Co., Ltd., Zhejiang (CN)

(72) Inventors: Jingsong He, Zhejiang (CN); Yiqin Cao, Zhejiang (CN); Li Feng, Zhejiang (CN); Xiaochang Leng, Zhejiang (CN); Jianping Xiang, Zhejiang (CN)

(73) Assignee: Hangzhou ArteryFlow Technology Co., Ltd., Hangzhou (CN)

(*) Notice: Subject to any disclaimer, the term of this patent is extended or adjusted under 35 U.S.C. 154(b) by 350 days.

(21) Appl. No.: 17/976,511

(22) Filed: Oct. 28, 2022

(65) Prior Publication Data
US 2023/0139405 A1    May 4, 2023

(30) Foreign Application Priority Data
Nov. 3, 2021  (CN) .......................... 202111295618.1

(51) Int. Cl.
  *A61B 6/50*  (2024.01)
  *A61B 6/00*  (2024.01)
  *G06T 7/174*  (2017.01)
(52) U.S. Cl.
  CPC .............. *A61B 6/504* (2013.01); *A61B 6/481* (2013.01); *G06T 7/174* (2017.01); *G06T 2207/30016* (2013.01); *G06T 2207/30104* (2013.01)
(58) Field of Classification Search
  CPC ......... A61B 6/504; A61B 6/481; A61B 6/507; A61B 5/026; A61B 5/0285; G06T 2207/30016; G06T 2207/30104; G06T 2207/30101
  See application file for complete search history.

(56) References Cited

U.S. PATENT DOCUMENTS

2016/0015348 A1*  1/2016  Ohishi ................... A61B 6/481
                                                600/431
2017/0076467 A1*  3/2017  Mistretta ............... G06T 11/008

OTHER PUBLICATIONS

Hoffman, Carson, et al. "A technique for intra-procedural blood velocity quantitation using time-resolved 2D digital subtraction angiography." Cvir Endovascular 4 (2021): 1-10. (Year: 2021).*

* cited by examiner

*Primary Examiner* — Raphael Schwartz (57) ABSTRACT

A stenosis assessment method and device based on the intracranial digital subtraction angiographic (DSA) imaging, including acquiring the intracranial DSA imaging and extracting two planar images containing the target blood vessel from the DSA imaging, wherein the two planar images have different shooting angles. According to the two planar images, a 3D model of the target vessel is established. Based on the established 3D model of the target vessel and the DSA imaging, the hemodynamic simulation of the target vessel is performed. The disclosure realizes the functional assessment of intracranial vascular stenosis, improves the diagnostic accuracy, and provides certain assistance for neurologists to determine intervention means. The disclosure of noninvasive FFR technology in the assessment of intracranial vascular stenosis can only rely on angiography for functional assessment, saving the medical examination cost of patients. It has more convenient operation and higher repeatability.

10 Claims, 5 Drawing Sheets

Acquire the DSA imaging of intracranial vessels and extract two planar images containing the target blood vessel from the DSA imaging, wherein the two planar images have different shooting angles  — S110

Based on the two planar images, a 3D model of the target vessel is built  — S120

Based on the established 3D model of the target vessel and the DSA imaging, the hemodynamic simulation of the target vessel is performed to derive specified stenosis assessment parameters for the target vessel which include at least one of the following: mean flow velocity, mean flow, pressure gradient, and blood pressure ratio  — S130

FIG. 9

STENOSIS ASSESSMENT METHOD AND DEVICE BASED ON INTRACRANIAL DSA IMAGING

CROSS-REFERENCE TO RELATED APPLICATIONS

This application claims priority from the Chinese patent application 2021112956181 filed Nov. 3, 2021, the content of which are incorporated herein in the entirety by reference.

TECHNICAL FIELD

This application relates to the field of medical technology specifically to one method and device for stenosis assessment based on intracranial DSA imaging.

BACKGROUND

In recent years, the number of deaths from cardio cerebrovascular disease worldwide is up to 15 million people each year, ranking first for various causes of death, and moreover, the younger trend of cardiovascular and cerebrovascular diseases tends to increase year by year. In cardiovascular and cerebrovascular diseases, ischemia of myocardial and cerebral tissue due to blockage of blood vessels is an important challenge in the clinic, and in the field of coronary artery, clinical technology has been transformed from simple assessment of stenosis degree to functional assessment, and FFR technology has been widely used in the clinical diagnosis of coronary disease.

Unfortunately, in the field of stroke, it still remains to evaluate whether the cerebral tissue is ischemic by visual vascular stenosis (such as diameter stenosis rate, area stenosis rate, minimum lumen area, etc.). From the perspective of hemodynamics, whether the tissue is ischemic is determined by the geometric shape of the vessel and the blood flow status in the vessel. It is possible to make a false diagnosis of ischemia solely based on the degree of stenosis. This problem has been confirmed in the coronary field, which also leads to the increasingly extensive application of FFR technology in the assessment of coronary stenosis.

SUMMARY

In response to the above problems, the present application embodiments provide a method and device for stenosis assessment based on intracranial DSA imaging.

In the first aspect, a stenosis assessment method based on intracranial DSA imaging is provided, which includes:
Acquire intracranial DSA(Digital Subtraction Angiography) imaging and extracting two planar images containing a target vessel from the described DSA imaging which have different shooting angles;
Build a 3D model of the target vessel based on the two planar images described;
Based on the established 3D model of the target vessel and the DSA imaging, the hemodynamic simulation of the target vessel is performed to derive specified stenosis assessment parameters which include at least one of the following: mean flow velocity, mean flow, pressure gradient, and blood pressure ratio.

Optionally, in the above method, the intracranial DSA imaging is acquired and two planar images containing the target vessel are extracted from the described DSA imaging which have different shooting angles, including:

Acquire intracranial DSA imaging taken at different angles in two groups;
Respectively take the frame with the lowest second average gray scale in each DSA image as the key frame;
Extract the enhanced features of the two key frames to obtain the skeleton of the vascular tree;
Determine the starting point and ending point of the target vessel, cut the target vessel from the vascular tree skeleton image to obtain two planar images containing the target vessel.

Optionally, in the method described above, extract the enhanced features of the two key frames to obtain the skeleton of the vascular tree, including:

The two key frames are successively processed by Gaussian smoothing, resampling, Hessian matrix enhancement, binarization, and corrosion algorithm thinning to obtain the skeleton of the vascular tree.

Optionally, in the method described above, the 3D model of the target vessel is built based on the two planar images described, including:

Extract the center and boundary lines of the target vessel in each planar image, respectively;
Determine the matching relationship of the center line of the target vessel in two planar images and determined the 3D center line in 3D space according to the matching relationship;
Determine a 3D model of the target vessel in terms of a 3D central line of the target vessel, and the matching relationships described.

Optionally, in the method described above, the center and boundary lines of the target vessel in the respective planar images are extracted, including:

For one planar image, determine the starting and ending points of the target vessels;
Employ a minimum path algorithm and identify a central line between the starting point and the ending point as the central line of the target vessel;
Determine multiple sample points on a centerline;
At the determined multiple sampling points, the planar image is resampled along the normal direction of the centerline to obtain the resampled image;
In the resampled image, the boundary intensity value of each sampling point is determined to obtain the boundary intensity image;
In the boundary intensity image, the minimum path algorithm is used to determine two boundary lines corresponding to the centerline.

Optionally, in the method described above, the specified stenosis assessment parameter is mean flow velocity;
Based on the established 3D model of the target vessel and the DSA imaging, the hemodynamic simulation of the target vessel is performed to derive specified stenosis assessment parameters, including:
From the DSA imaging described, the start and end frames of the contrast agent flow through the target vessel are determined; And the mean blood flow velocity is determined according to the following formula:

$$V=L/((F2-F1)/fps);$$

Where, V is the mean blood flow velocity, L is the target vessel length, fps is the frame rate of the DSA imaging, F1 is the frame number of the starting frame, F2 is the frame number of the ending frame;

Optionally, in the method described above, the specified stenosis assessment parameter is mean blood flow;
Based on the established 3D model of the target vessel and the DSA imaging, the hemodynamic simulation of the target vessel is performed to derive specified stenosis assessment parameters, which also includes:

Discrete the 3D model of the target vessel into multiple 3D center points;

Determine the length from each 3D center point to the starting point of the target vessel, as well as the corresponding vessel cross section area of each center point; The mean blood flow is determined according to the following formula:

$$Q = V * \int_{i=1}^{N1} S_i/N1;$$

Where, V is the mean blood flow velocity within the target vessel and $S_i$ is the vessel cross-sectional area corresponding to the i-th 3D center point, N1 is the amount of 3D center points.

Optionally, the specified stenosis assessment parameter is blood pressure gradient;

Based on the 3D model of the target vessel and the DSA imaging, the hemodynamic simulation of the target vessel is performed to derive specified stenosis assessment parameters, which also includes:

For a 3D center point, the following formula is used to determine the pressure drop of the 3D center point relative to the starting point:

$$DP_i = a*V + b*V^2 + c*V;$$

Where, $DP_i$ is the pressure drop at the i-th 3D center point relative to the origin of the target vessel, a is the viscous loss coefficient, b is the distension loss coefficient, and c is the Bernoulli coefficient;

The determined pressure drop of each 3D center point forms the blood pressure gradient, PG.

Optionally, in the method described above, the specified stenosis assessment parameter is blood pressure ratio;

Based on the established 3D model of the target vessel and the DSA imaging, the hemodynamic simulation of the target vessel is performed to derive specified stenosis assessment parameters, which also includes:

Determined the blood pressure ratio according to the following formula:

$$PR = 1 - PG/Pa;$$

Where, PR is the blood pressure ratio, PG is the blood pressure gradient, and Pa is the proximal pressure of the lesion taken in the catheterization laboratory.

In the second aspect, an intracranial vessel is provided with a blood flow status assessment device comprising:

Image processing unit is configured to acquire intracranial DSA imaging and extract two planar images of the key frames of the target vessel from the DSA imaging which have different shooting angles;

Model building unit is configured to build a 3D model of the target vessel from the two planar images described;

The numerical simulation unit is configured to simulate the hemodynamics of the target vessel based on the established 3D model to derive specified stenosis assessment parameters which include at least one of the following: mean flow velocity, mean flow, pressure gradient, and blood pressure ratio.

In the third aspect, the present application embodiments also provide an electronic device comprising: a processor, a memory arranged to store computer executable instructions which, when executed, cause the processor to carry out any of the above methods.

In the fourth aspect, the present application embodiments also provide a computer-readable storage medium storing one or more programs which, when executed by an electronic device comprising multiple applications, makes the described electronic device perform any of the above methods.

At least one of the above technical schemes adopted by the embodiments of the present application is capable of achieving the following beneficial effects:

This application applies by acquiring the intracranial DSA imaging and extracting two planar images containing the target blood vessel from the DSA imaging, wherein the two planar images have different shooting angles; According to the two planar images, a 3D model of the target vessel is established; Based on the established 3D model of the target vessel and the DSA imaging, the hemodynamic simulation of the target vessel is performed to derive specified stenosis assessment parameters which include at least one of the following: mean flow velocity, mean flow, pressure gradient, and blood pressure ratio. Based on the intracranial DSA imaging, the application reconstructs the 3D model of the diseased vessel, and estimates the stenosis assessment parameters in combination with the patient specific blood flow parameters, including but not limited to the mean blood flow velocity, mean blood flow, blood pressure gradient, and blood pressure ratio. First, the application realizes the functional assessment of intracranial vascular stenosis, improves the diagnostic accuracy, and provides certain assistance for neurologists to determine intervention means; Second, the application of noninvasive FFR technology in the assessment of intracranial vascular stenosis can realize functional assessment only rely on angiography, saving the medical examination cost of patients; Third, compared with the coronary noninvasive FFR technique, the present application achieves automated image identification as well as automated mean blood flow velocity estimation, which is more convenient and reproducible.

BRIEF DESCRIPTION OF THE DRAWINGS

The drawings illustrated here are used to provide further understanding of this application, form part of this application, and the schematic embodiments of this application and their instructions are used to explain the application and do not constitute an improper qualification of the application. In the drawings.

DESCRIPTION OF THE EMBODIMENTS

To make the purpose, technical scheme, and advantages of this application clearer, the technical scheme of this application will be clearly and completely described below in combination with the specific embodiments and the corresponding figures. It is obvious that the embodiments described are only part, not all, of the present application. Based on the embodiments in this application, all other embodiments obtained by persons of ordinary skill without making the premise of creative labor fall within the scope of the protection of this application.

The following, in combination with embodiments and accompanying figures, details of the technical scheme will be provided.

Figure 1:
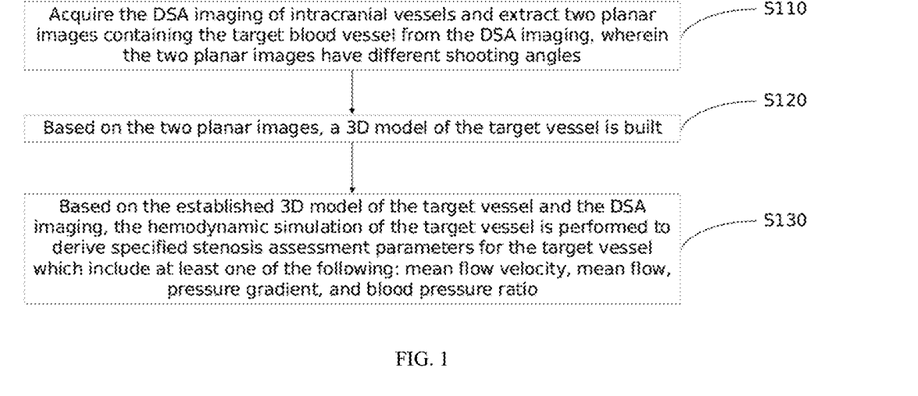
FIG. 1 shows a flowchart of one embodiment of the present application.

FIG. 1 shows the flowchart according to one embodiment of the present application, from FIG. 1, it can be concluded that the present application includes at least steps S110~S130:

S110: acquire intracranial DSA imaging, and extract two images containing the target vessel from the DSA imaging, where the two selected images have different shooting angles.

The blood flow assessment method of the application is based on a 3D model. First, it is necessary to establish a 3D model of the target vessel, which is based on DSA images obtained in angiography technology. The first choice is to obtain intracranial DSA image, which can be understood as a video stream, and the video stream is composed of continuous multi frame images. In angiography technology, in order to enable the machine to "see" blood vessels, it is necessary to inject contrast agents into the blood vessels. When the contrast agent fills the diseased vessels, it is the most ideal state.

This most ideal state can be defined as the keyframe. While intracranial DSA angiography, a portion of the X-ray is absorbed when the iodine containing contrast agent flows into the vessel, resulting in the vessel becoming darker in the image, and therefore, when the contrast agent is full of the vessel, that is, when the contrast is sufficient, the second average gray scale of that frame will reach the minimum, that is, the frame with the lowest second average gray scale can be understood as the keyframe.

To achieve a relatively desirable effect, subsequent steps can be performed on the keyframe. In the subsequent process of 3D model building, it is required to acquire at least two images with different shooting angles, for which, two DSA imaging with different shooting angles need to be selected, repeating the determination step of the above keyframes to obtain two keyframes, as the mentioned selected images containing the target vessel.

This "acquisition" process, which can be understood as receiving, is enabled by staff input. It needs to be stated that, these two selected images have different angles of angiography. Otherwise, the acquired images are the same, not in the sense of "fusion", if they have the same angle. For a better effect, in some embodiments of the present application, the difference in angle between the two selected images is not less than 25°

S120: Based on the two selected images, a 3D model of the target vessel is built.

Make the "fusion" of the above two selected images to build a 3D model of the target vessel.

In some embodiments of the present application, the following steps can be taken for 3D model building: the center and boundary lines of the target vessel in each selected image are extracted separately; Determine the matching relationship of the center lines of the target vessel in two selected images, and then determine the 3D center line of the target vessel in 3D space according to the matching relationship; A 3D model of the target vessel is determined in terms of the 3D centerline and the matching relationships described.

Vessels are "earthworm" like in the selected images, or it can also be understood as irregular "tube" like, using image recognition techniques, to process each image to get the center line and boundary lines of the target vessel, it needs to be stated that the center line and boundary lines are also irregular.

For the recognition of the center and boundary lines, it can be achieved refer to image recognition techniques. As first binarization of the image and then identifies two boundary lines for the target vessel, taking the line at the middle of the two boundary lines as the center line.

Then fused the target vessel in the two selected images in a coordinate system of 3D space to form the 3D model of the vessel. In the present application, the 3D center line of the vessel is got first, and then surround the 3D center line to determine the 3D model of the target vessel.

Firstly determined the matching relationship of the center lines in the two selected images, in some embodiments of the present application, the center lines of target vessel in two images are discretized into multiple corresponding pairs of center points based on the definition of epi-polar constraint in the binocular vision algorithm.

Scored the two selected images as the first and second image, respectively, and the target vessel in the first image scored as the first vessel, the target vessel in the second image scored as the second vessel.

Suppose there are multiple first center points $P_i$ in the first vessel and multiple second center points $Q_i$ in the second vessel, and the first center point $P_i$ of the first vessel corresponds to the second center point $Q_i$ of the second vessel, thus forming the matching relationship between the two center lines of the target vessel in the two selected images.

To improve modeling accuracy, it is possible to discretize the center lines into as many center point pairs as possible.

Determined the 3D center line of the target vessel in 3D space based on the matching relationship of the center lines of the two selected images.

Specifically, in some embodiments of the present application, the X-ray source point positions in two selected images are determined firstly; Multiple spatial 3D points of the target vessel are determined from the location of the source point and the center point pairs; The multiple spatial 3D points are connected with a smooth curve, resulting in the 3D centerline.

Assumed that when reading the angiography images, the X-ray source points $O_1$, $O_2$ can be determined, connecting the rays $O_1P_i$, $O_2Q_i$, in two images respectively, the intersection of the two rays is the spatial 3D point corresponding to $P_i$ and $Q_i$. One by one, the paired center point pairs are subjected to the above operations, and a 3D center line of the target vessel could be obtained.

In some embodiments of the present application, the matching relationship of the center lines of the target vessel in two images also includes four matching boundary points corresponding to each pair of center points, and the specific methods of determination are: for one center point on a center line, along the normal direction, two matching boundary points on the two boundary lines are calculated corresponding to the center line, and for another center point of the pair, two matching boundary points are determined with the same method, so that the four matching boundary points defines the relationship between the center point pair to the four boundary lines. The role of this matching boundary points is to prepare the 3D boundary lines for building a 3D model in the follow-up. With the method described above, multiple center point pairs on two center lines are identified with 4 matching points to the boundary lines.

Determined the 3D model of the target vessel around the 3D centerline after obtaining which in 3D space, i.e. boundary lines of this 3D centerline needs to be determined.

Specifically, four matching boundary points corresponding to the respective center points are projected into one cross section in 3D space; The projection points of four matched boundary points in the same cross-section are closed, resulting in the contour of the target vessel of that cross-section; The resulting contours of the target vessel of each cross-section are connected to obtain a 3D model of the target vessel.

Projected these four matched boundary points on the same cross-section surrounding a 3D center point, result in four projected points, and then closed the four projected points in the same cross-section, with the caveat that it is best to use a curve fitting approach for closure. Doing the above for all of the center point pairs separately result in multiple "annular" contours surrounding the 3D center line, and the resulting contours of the target vessel for each cross-section are then connected, result in a 3D model of the target vessel.

S130: Based on the established 3D model of the target vessel and the two DSA imaging, the hemodynamic simulation of the target vessel is performed to derive specified stenosis assessment parameters which include at least one of the following: mean flow velocity, mean flow, pressure gradient, and pressure ratio.

After establishing a 3D model of the target vessel, hemodynamic simulation can be performed on the basis of the 3D model, thereby introducing FFR (fractional flow reserve)—related techniques into intracranial stenosis assessment.

Specifically, it is possible to estimate the relevant parameters of FFR such as mean flow velocity, mean flow, pressure gradient and pressure ratio, where mean flow, pressure gradient as well as pressure ratio are based on mean flow velocity.

In some embodiments of the present application, the mean blood flow velocity estimation can take the following approach: to accurately estimate the mean blood flow velocity, the start frame F1 and end frame F2 must be recognized firstly, after the target vessel is selected manually. F1 is identified the frame that the contrast agent just reached the starting point of the target vessel, and F2 is identified the frame that the contrast agent just reaching the ending point, and then the mean blood flow velocity V is calculated by:

$V = L/((F2-F1)/fps);$

Where L is the 3D target vessel length, which can be calculated as the 3D center line length, and fps is the frame rate of the DSA imaging, which can be read from the image label.

Figure 7A:
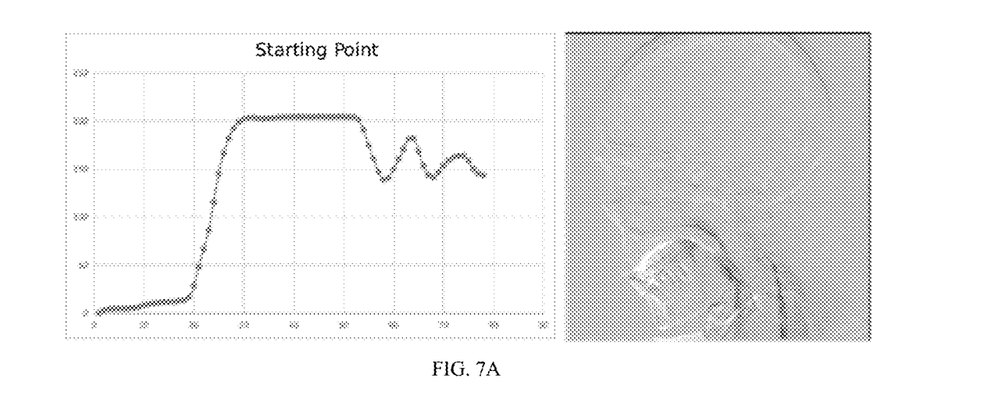
FIGS. 7A-7B show start and end frame images of contrast agent flow through a vessel, as well as the time-concentration curve of contrast agent according to one embodiment of the present application.
Figure 7B:
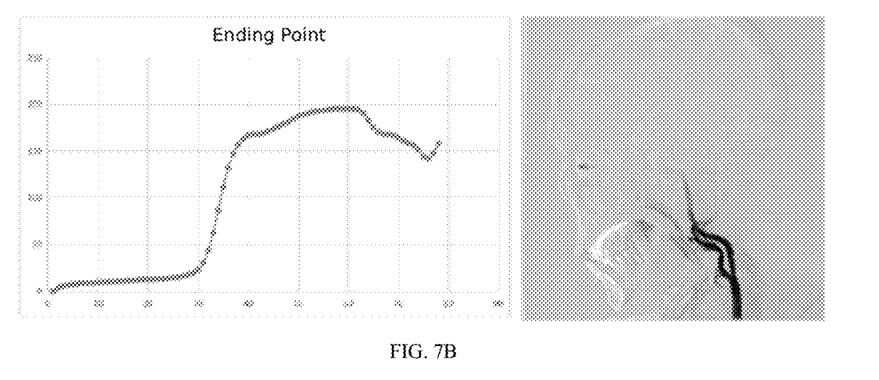

Please refer to FIGS. 7A-7B, which show the start and end frame images of contrast agent flow through the vessel, and the contrast agent time-concentration curve according to one embodiment of the present application. For the calculation of F1, after determining the coordinates of the starting point on the DSA image, a first average gray scale is calculated, which is the average of pixel value over an area of n*n range with the starting point as center point in the DSA imaging. In particular, n can take the value of 3, 5, or 7. For the DSA image sequences, the first average gray scale of the starting point is calculated frame by frame, and then the first average gray scale of the corresponding image in each frame is subtracted separately by the first average gray scale of the first image to obtain the corresponding contrast agent concentration in each frame, in chronological order, and finally, the contrast agent time-concentration curve of the starting point is obtained. A maximum value point Imax is searched on the curve, based on which the contrast influx marker threshold is set σ, This threshold is calculated as: σ=a*Imax, where a is the weight coefficient taking values ranging from 0.1-0.5.

After assessment of marker thresholds σ, on the contrast time-concentration curve, search for the first point greater than or equal to σ on the curve, the number of imaging frame corresponding to the point is the start frame F1, the end frame F2 can be obtained similarly.

The calculation of other parameters can then be performed, in some embodiments of the present application, the calculation of the mean flow of blood can be performed with the following method: discretizing the 3D model of the target vessel into multiple 3D center points;

Determined the length of each 3D center point to the start of the target vessel, and the area of each cross-section corresponding to the center points; And the mean blood flow is calculated according to the following formula:

$$Q = V * \int_{i=1}^{N1} S_i/N1;$$

Where, V is the mean velocity within the target vessel and $S_i$ is the vessel cross-sectional area corresponding to the i-th 3D center point, N1 is the amount of 3D center points.

Based on the mean velocity and 3D model of the target vessel, hemodynamic parameters such as mean flow Q, pressure gradient PG as well as pressure ratio PR can be calculated for the target vessel.

Specifically, the target vessel 3D model is discretized into multiple 3D center points, assuming that the target vessel 3D center line consists of $P_1, P_2 \ldots P_N$ total N center points, then the length of each point to the starting point can be calculated one by one as $L_1, L_2 \ldots L_N$, and each center point corresponds to the vessel cross-sectional area $S_1, S_2 \ldots S_N$.

The mean flow Q is calculated as:

$$Q = V * \int_{i=1}^{N} S_i/N$$

Where V is the intravascular mean flow velocity and $S_i$ is the vessel cross-sectional area corresponding to the i-th center point.

In some embodiments of the present application, in the process described above, the pressure gradient may be determined using:

For one 3D center point, the pressure drop at this 3D center point relative to the start of the target vessel is determined using the formula:

$DP_i = a*V + b*V^2 + c*V,$

Where, $DP_i$ is the pressure drop at the i-th 3D center point relative to the start of the target vessel, a is the viscous loss coefficient, b is the distension loss coefficient, and c is the Bernoulli coefficient.

Determined the pressure drop at each 3D center point, forming the described blood pressure gradient PG.

Specifically, for either center point $P_i$, combined with the length to the start point $L_i$ and the vessel cross-sectional area $S_1$-$S_i$, the pressure drop at this point relative to the start of the target vessel $DP_i$ can be calculated as:

$$DP_i = a*V + b*V^2 + c*V;$$

Where a is the viscous loss coefficient, determined by blood viscous versus vessel geometry, b is the distension loss coefficient, determined by the degree of vessel stenosis, and c is the Bernoulli coefficient, determined by vessel entry and exit morphology.

Calculated its corresponding pressure drop for all center points to obtain the pressure gradient PG of the whole target lesion vessel, i.e., $PG = DP_N$.

In some embodiments of the present application, in the process described above, the described blood pressure ratio may be determined employing the method described below; The blood pressure ratio is determined according to the following formula:

$$PR = 1 - PG/Pa,$$

Where PR is the blood pressure ratio, PG is the blood pressure gradient, and Pa is the proximal pressure across the lesion taken in the catheterization laboratory.

If the pressure Pa proximal to the lesion is accessible in the catheterization laboratory, the pressure ratio PR is calculated as:

$$PR = 1 - PG/Pa,$$

If accurate value for Pa could not be obtained, Pa is taken to be 90 mmHg by default.

As can be seen from the method shown in FIG. 1, the present application applies by acquiring intracranial DSA image sequences, and extracting two selected images containing the target vessel from the described DSA image sequences, which have different shooting angles; Based on the two selected images described, a 3D model of the target vessel is build; Based on the established 3D model of the target vessel and the DSA image sequences, the hemodynamic simulation of the target vessel is performed to derive specified stenosis assessment parameters for the target vessel which include at least one of the following: mean flow velocity, mean flow, pressure gradient, and pressure ratio. This application is based on intracranial DSA angiography, the reconstruction of a 3D model of the diseased vessel, and the incorporation of patient specific flow parameters to estimate stenosis assessment parameters, including but not limited to mean flow velocity, mean flow, pressure gradient, and pressure ratio. First, based on intracranial DSA angiography, this application achieves the functional assessment of intracranial vascular stenosis, improves the diagnostic accuracy, and provides a certain auxiliary role for neurologists to determine the means of intervention; Second, the application of this section applied coronary non-invasive FFR technology in the assessment of intracranial vascular stenosis, and only angiography is necessary, which reduces the cost of medical examination for patients; Third, compared with the coronary non-invasive FFR technique, the present application achieves automated image identification as well as automated mean blood flow velocity estimation, which is more convenient and reproducible.

In some embodiments of the present application, the following method can also be taken for the extraction of center lines and boundary lines in selected images: for one selected image, the starting and ending points of the target vessel are determined; Using a minimum path algorithm, a center line between the starting point and the ending point can be identified; Determination of multiple sampling points on the center line; At multiple sampling points identified, the selected image is resampled along the normal direction to give a new resampled image; In the resampled image described, the boundary intensity value of each sampling point is determined to obtain the boundary intensity image; In the described boundary intensity image, a minimum path algorithm is employed, two boundary lines corresponding to the described center line can be identified.

Specifically, for a target vessel in one image, the target lesion vessel starting and ending points can be manually selected, and the initial center line of the target vessel can be extracted by applying the Dijkstra minimum path algorithm. Resampled image is obtained by resampling keyframe image in the normal direction of the center line. In the resampled image, the boundary intensity value is calculated point by point to obtain the boundary intensity image, in which the minimum path algorithm is used to search the two vessel boundary lines corresponding to the center line, reflected the boundary lines back into the original image, then all the center line and boundary lines are extracted to completion.

In some embodiments of the present application, the determination of the two matched boundary points corresponding to the center point includes: Determine the normal vector of the center point, and make rays along the direction of the normal vector; The two intersection points between the two boundary lines and the ray are regarded as the two matching boundary points corresponding to the center point.

That is, in determining the matching of the boundary points to the center point, for a center point, first determine its normal direction and then make a ray along the normal direction, and the intersection of the ray with the two boundary lines, is the matching point corresponding to that center point. For one center point pair, four matching boundary points are corresponding.

In some embodiments of the present application, some vessels are particularly curved and there may be more than one intersection of a ray with a boundary line, the intersection with the closest distance from the center point is taken as the matching point.

Figure 2:
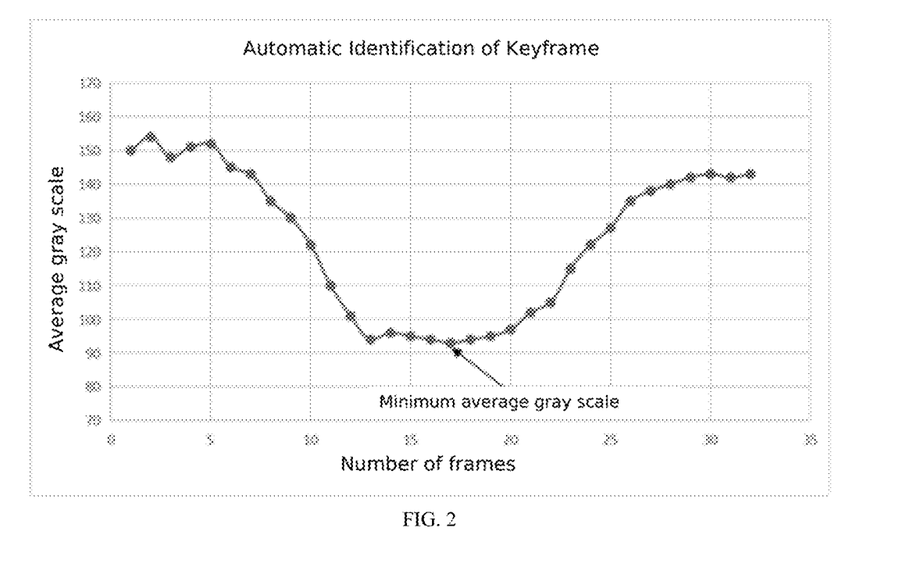
FIG. 2 shows a calculated curve according to the second average gray scale in one embodiment of the present application.

A further example of this application is given below and the process may be briefly described as follows:

First, keyframe extraction: after importing DSA image sequences, calculate the image second average gray scale frame by frame, if the image size is M*N, and the total number of frames of the image is K, then the second average gray scale is calculated as:

$$I_k = \Sigma_{i=1}^{M} \Sigma_{j=1}^{N} I(i,j)/(M*N),$$

Where $I_k$ is the second average gray scale of the k-th frame image, and I(i, j) is the gray scale at the k-th frame image coordinates (i, j). In intracranial DSA angiography, when the iodized contrast agent flows into the blood vessel, it will absorb part of the X-ray, causing the blood vessel to become darker in the image. Therefore, when the contrast agent fully flows into and fills the blood vessel, that is, when the angiography is sufficient, the second average gray scale of the frame will reach the minimum value. Specifically, the key frame O is defined as: $O = \arg\min (I_k)$, wherein the operator arg min is represents the value of the argument when the minimum value of I_k is reached; that is, the frame with the lowest second average gray scale in all image frames, as shown in FIG. 2, which shows the calculation result curve of the second average gray scale in an embodiment of the application, in which the frame with the lowest second average gray scale is taken as the key frame.

Figure 3A:
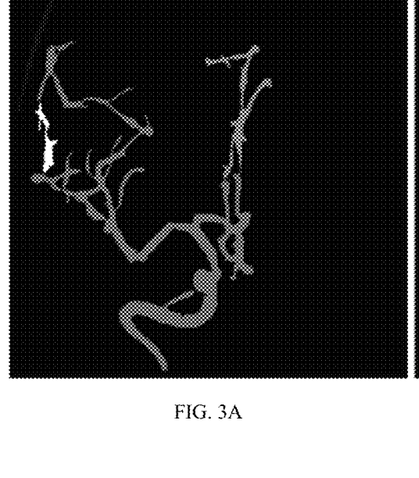
FIGS. 3A-3B show the vascular tree skeleton diagram of the vessels at two different shooting angles.
Figure 3B:
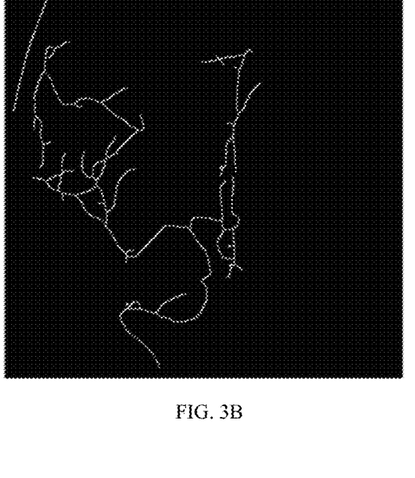

Second, image processing: after extracting the key frame image, the image is first Gaussian smoothed and the image is uniformly resampled to 512*512, followed by application of the Hessian matrix to reinforce the tubular vascular structure. After the enhanced vessel images are obtained, the whole image is binarized using the thresholding method, and the approximate morphology of the whole vessel tree could be extracted, followed by the refinement treatment of the vessel tree using the corrosion algorithm, finally resulting in the whole vessel tree skeleton diagram, as shown in FIGS. 3A-3B, which show the vascular tree skeleton diagram of the target vessel at two different shooting angles.

Figure 4A:
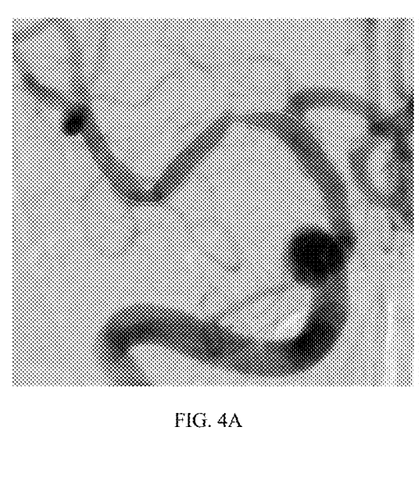
FIGS. 4A-4B show the resulting images containing the target vessel after feature extraction from two different shooting angles according to one embodiment of the present application.
Figure 4B:
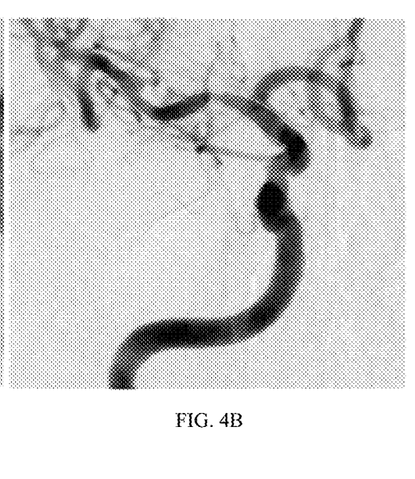

Third, feature extraction: after obtaining the central line of the entire vascular tree, i.e., the skeleton map, the starting point, ending point of the target lesion vessel are manually selected, and the initial central line of the target vessel could be extracted by applying the Dijkstra minimum path algorithm. Resampled images are obtained by resampling keyframe images in the normal direction of the center line. In the resampled images, the boundary intensity value is calculated point by point, resulting in the boundary intensity image, in which the minimum path algorithm is used to search the two vessel boundary lines corresponding to the center line, reflecting the boundary lines back into the original image, then all the center line, boundary lines are extracted to completion. FIGS. 4A-4B show two result images containing the target vessel obtained after image feature extraction from two different selected images according to one embodiment of this application.

Fourth, epipolar constraint: after two intracranial DSA image sequences with angle difference ≥25° are subjected to the above steps, two groups of center line and boundary lines can be obtained. In a 3D reconstruction method, the matching relationship between the two center lines needs to be determined. So, the center lines can be discretized into paired center points using the epipolar constraint in the binocular vision algorithm.

Fifth, the matching of center line and boundary lines: after obtaining two groups of matching center lines, the center lines of the two perspectives are matched with the boundary lines, respectively. Specifically, for each center point $P_i$ on the center line, its normal vector is calculated, a straight line over $P_i$ along the normal vector is taken, and the intersection of this line with the two boundary lines is then the matching points of the boundary lines with the center point $P_i$, which is denoted as $L_i$, $R_i$, respectively.

Specifically, when vessel distortion is severe, there may be multiple intersection points to be taken at a boundary line, calculating the distance from the center point separately, taking the closest point as the matching point $L_i$ or $R_i$.

Figure 5:
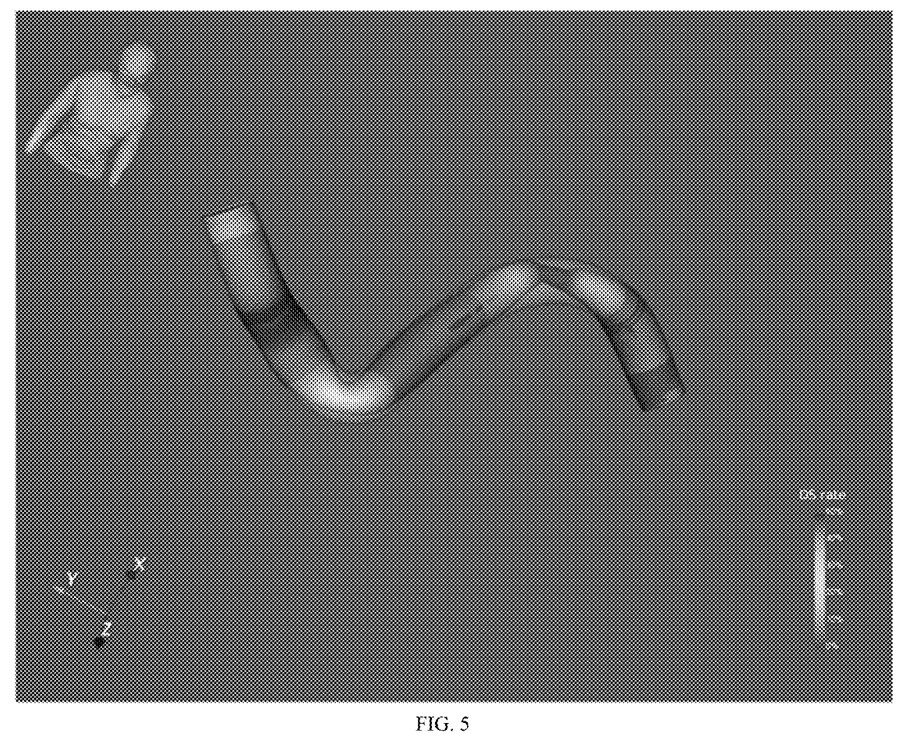
FIG. 5 shows a 3D model of the target vessel according to one embodiment of the present application.

Sixth, 3D reconstruction: after completing the first two-step matching operation, the matching relationship between the two center lines is obtained, keeping in mind that the first image center point $P_i$ corresponds to the second image center point $Q_i$. When reading DSA image, the X-ray source points $O_1$, $O_2$ of the two images are available, connecting rays $O_1 P_i$, $O_2 Q_i$, the intersection of the two rays is the spatial 3D point corresponding to $P_i$ and $Q_i$. Performing the above operations on the paired center points one by one, we can obtain the 3D center line of the target vessel, and then project the four two-dimensional boundary points corresponding to each center point into the 3D space, which can obtain four boundary points of each cross-section, using the B-spline curve to sequentially close the four spatial boundary points, so that the vessel contour on this section can be obtained. After the vessel contours are found on all the sections, the target vessel 3D reconstruction is completed as shown in FIG. 5, which shows the 3D model of a target vessel according to one embodiment of the present application.

Figure 6:
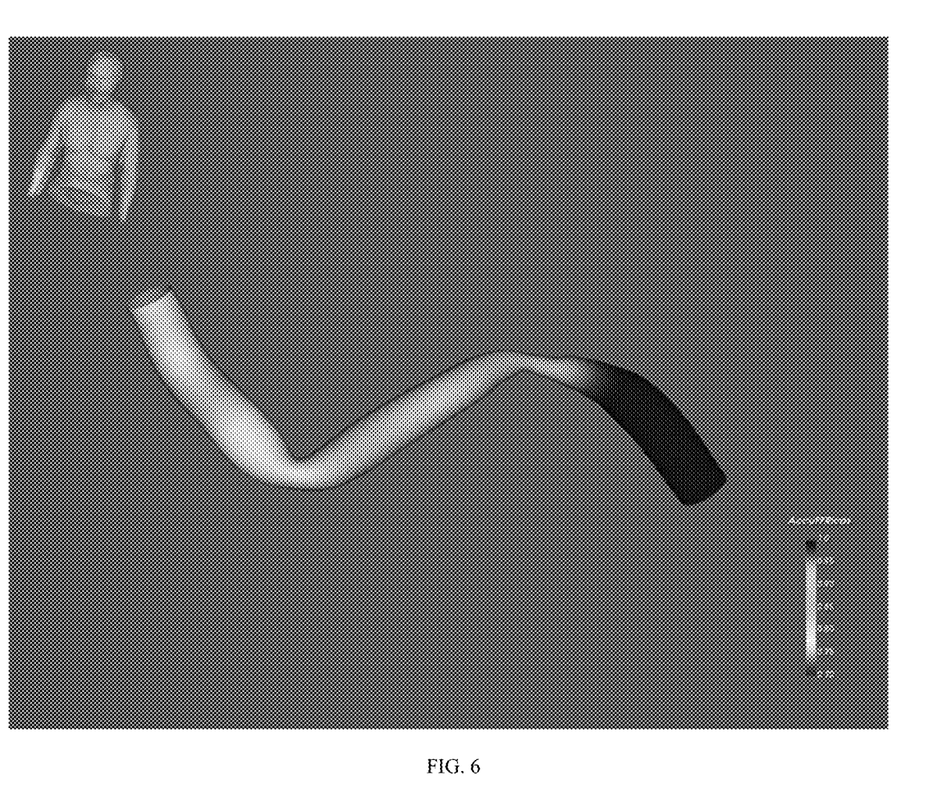
FIG. 6 shows a visual image of the distribution of calculated results for the pressure ratio of the target vessel according to one embodiment of the present application.

Seventh, the mean blood velocity estimation, as shown in FIG. 6, which shows a visual image of the distribution of calculated results for the pressure ratio of the target vessel according to one embodiment of the present application.

Figure 8:
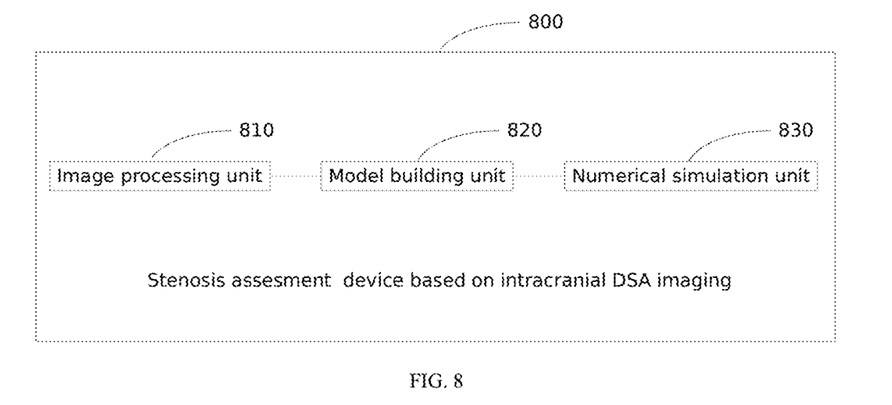
FIG. 8 shows a structural schematic of the device according to one embodiment of the present application.

FIG. 8 illustrates a device for the present application according to one embodiment, the device 800 includes:

Image processing unit 810, which is used to acquire intracranial DSA image sequences and extract two images of the keyframes and the two described images have different shooting angles;

Model building unit 820, which is used for building a 3D model of the target vessel according to the two selected images described;

The numerical simulation unit 830, which is used for the hemodynamics simulation of the target vessel based on the established 3D model to derive specified stenosis assessment parameters which include at least one of the following: mean flow velocity, mean flow, pressure gradient, and pressure ratio.

In some embodiments of the present application, in the device mentioned above, an image processing unit 810 is used to acquire two groups of intracranial DSA imaging with different shooting angles; One frame with the lowest second average gray scale in each DSA image is taken as the keyframe, respectively; The resulting two keyframes are subjected to enhanced feature extraction, acquiring a vascular tree skeleton map; The starting and ending points of the target vessel are determined, and the target vessel is cut from the vascular tree skeleton map to obtain two planar images containing the target vessel.

In some embodiments of the present application, in the device mentioned above, image processing unit 810 is used to sequentially perform Gaussian smoothing, resampling, intensification of the Hessian matrix, binarization, and refinement of the corrosion algorithm on the two keyframes to obtain a vascular tree skeleton map.

In some embodiments of the present application, in the device mentioned above, the model building unit 820 is used to extract the center and boundary lines of the target vessel in the two selected images, respectively; Determine the matching relationship of the two center lines of the target vessel, and determine the 3D center line of the target vessel in 3D space according to the matching relationship; A 3D model of the target vessel is determined in terms of the 3D centerline and the matching relationships described.

In some embodiments of the present application, in the above device, the model building unit 820 is used to determine the starting point and the ending point of the target vessel for a selected image; using the minimum path algorithm to determine the centerline between the starting and ending points as the centerline of the target vessel; determine multiple sampling points on the centerline; at the determined multiple sampling points, resampling the selected image along the normal direction of the centerline to obtain the resampled image; in the resampled image, determine the boundary intensity value of each sampling point to obtain the boundary intensity image; in the boundary intensity image, use the minimum path algorithm to determine two boundary lines corresponding to the center line.

In some embodiments of the present application, in the above device, the specified stenosis assessment parameters are the mean blood flow velocity; The numerical simulation unit 830 is used to determine the start frame and end frame of the contrast agent flowing through the target vessel according to the DSA imaging and determine the mean blood flow velocity according to the following formula:

$V=L/((F2-F1)/fps);$

Where, V is the mean blood flow velocity, L is the target vessel length, fps is the frame rate of the DSA image, F1 is the frame number of the starting frame in the DSA image, F2 is the frame number of the ending frame in the DSA image;

In some embodiments of the present application, in the above devices, the specified stenosis assessment parameters are blood mean flow; Numerical simulation unit 830, which is also used to discretize the 3D model of the target vessel into multiple 3D center points; Determine the length of each 3D center point to the origin of the target vessel, and the area of the vessel cross-section corresponding to each center point; And the mean blood flow is determined according to the following formula:

$$Q = V * \int_{i=1}^{N1} S_i/N1;$$

Where, V is the mean blood flow velocity within the target vessel and $S_i$ is the vessel cross-sectional area corresponding to the i-th 3D center point, N1 is the amount of 3D center points.

In some embodiments of the present application, in the device described above, the specified stenosis assessment parameters are blood pressure gradients; Numerical simulation unit 830, is also used to determine the pressure drop for a 3D center point relative to the origin of the target vessel with the following formula:

$DP_i = a*V + b*V^2 + c*V;$

Where, $DP_i$ is the pressure drop at the i-th 3D center point relative to the origin of the target vessel, a is the viscous loss coefficient, b is the distension loss coefficient, and c is the Bernoulli coefficient; The determined pressure drop at each 3D center point formed the mentioned blood pressure gradient, PG.

In some embodiments of the present application, in the above devices, the specified stenosis assessment parameters are blood pressure ratio; The numerical simulation unit 830, is also used to determine the blood pressure ratio according to the following formula:

$PR = 1 - PG/Pa,$

Where PR is the blood pressure ratio, PG is the blood pressure gradient, and Pa is the proximal pressure across the lesion taken in the catheterization laboratory.

It needs to be stated that the devices for intracranial stenosis assessment above may achieve the blood flow assessment methods mentioned above one by one.

Figure 9:
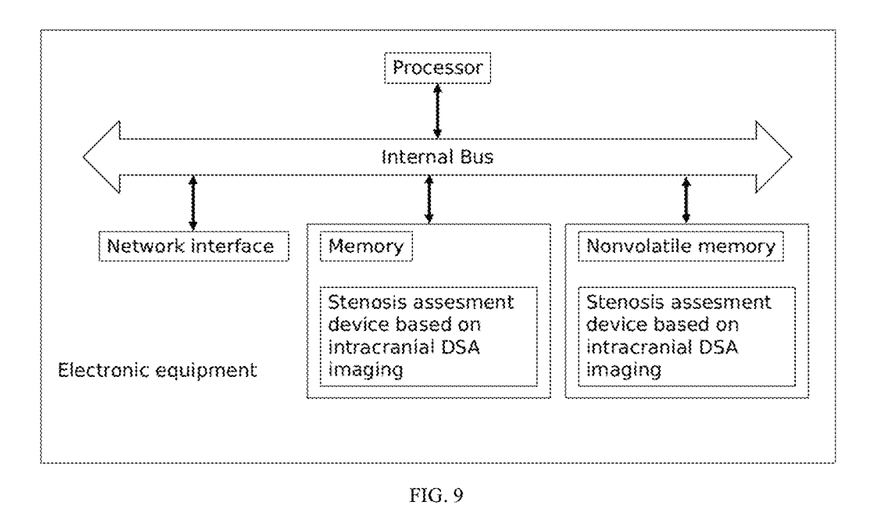
FIG. 9 shows a structural diagram of the electronic device according to one embodiment of the present application.

FIG. 9 is a schematic of the structure of an embodiment electronic device of the present application. Please refer to FIG. 9, at the hardware level, this electronic device includes a processor and, optionally, internal bus, network interface, memory, of which, the memory may contain memory, such as high-speed random access memory (RAM), or may also include non-volatile memory, such as at least 1 disk memory and so on. Of course, this electronic device may also include hardware required by other businesses.

The processor, network interface and memory can be interconnected by internal bus, which can be ISA (Industrial Standard Architecture), PCI (peripheral component interconnection, peripheral component interconnection standard) or EISA (extended industrial standard architecture, extended industrial standard architecture) and so on. The described bus can be divided into address bus, data bus, control bus and so on. For easy representation, it is represented by only one two-way arrow in FIG. 9, but it does not indicate only one bus or one type of bus.

Memory, for storage procedures. Specifically, the procedures may include a program code that includes computer operating instructions. The memory can include memory and nonvolatile memory with instructions and data provided to the processor.

Processor reads the corresponding computer program from nonvolatile memory into memory and then runs, forming on a logical level a stenosis assessment device based on intracranial DSA imaging. Processor, performs the procedures deposited by memory, and is specifically used to perform the following:

Acquired intracranial DSA image sequences and extracted two images containing the target vessel from the described sequences which are with different shooting angles;

Created a 3D model of the target vessel according to two selected images as described;

Based on the established 3D model of the target vessel and the DSA image sequences, the hemodynamic simulation of the target vessel is performed to derive specified stenosis assessment parameters for the target vessel which include at least one of the following: mean flow velocity, mean flow, pressure gradient, and pressure ratio.

The above method performed by a stenosis assessment device based on intracranial DSA imaging, as revealed by the embodiment shown in FIG. 8 can be applied in, or implemented by, a processor. The processor may be an integrated circuit chip, capable of processing signals. In the implementation process, the steps of the above methods can be accomplished by the integrated logic circuit of the hardware in the processor or by instructions in the form of software. The processors mentioned above can be general processors, including central processing unit (CPU), network processor (NP), etc; It can also be a digital signal processor (DSP), an Application Specific Integrated Circuit (ASIC), field programmable gate array (FPGA), or other programmable logic devices, discrete gates or transistor logic devices, or discrete hardware components. The disclosed individual methods, steps, and logic block diagram in embodiments of the application may be realized or executed. A generic processor may be a microprocessor or this processor may also be any regular processor, etc. The steps combined with the methods disclosed in the embodiment of this application can be directly performed by the hardware decipher processor execution or by a combination of the hardware and software modules in the decipher processor. The software module can be located in the mature storage medium, such as random memory, flash memory, read-only memory, programmable read-only memory, or electrical scrub programmable memory, registers, etc. This storage medium is located in memory, and the processor reads the information in memory, combining with its hardware completes the steps of the above method.

This electronic device also performs the methods of the intracranial stenosis assessment based on DSA image device in FIG. 8, and achieves the capabilities in the embodiment shown in FIG. 8, which are not further discussed in this application.

This application embodiment also proposes a computer-readable storage medium which stores one or more procedures comprising an instruction which, when executed by an electronic device comprising multiple applications, enables this electronic device to perform the methods performed by the stenosis assessment device based on intracranial DSA imaging in the embodiment shown in FIG. 8 and is specifically used to perform:

Acquired intracranial DSA image sequences and extracted two images containing the target vessel from the described sequences which are with different imaging angles;

Built a 3D model of the target vessel according to the two selected images;

Based on the established 3D model of the target vessel and the DSA image sequences, the hemodynamic simulation of the target vessel is performed to derive specified stenosis assessment parameters for the target vessel which include at least one of the following: mean flow velocity, mean flow, pressure gradient, and pressure ratio.

Those skilled in the field should understand that embodiments of the application can be provided as methods, systems, or computer program products.

Therefore, the present application may take the form of a complete hardware embodiment, a complete software embodiment, or an embodiment combining software and hardware aspects. Moreover, the present application may take the form of a computer program product implemented on one or more computer usable storage media (including but not limited to disk memory, CD-ROM, optical memory, etc.) containing computer usable program codes.

The application is described with reference to the flow chart and/or block diagram of the method, device (system), and computer program product according to the embodiments of the application. It shall be understood that each flow and/or block in the flow chart and/or block diagram and the combination of flow and/or block diagram can be realized by computer program instructions. These computer program instructions can be provided to a processor of a general computer, a special computer, an embedded processor, or other programmable data processing device to produce a machine such that instructions executed by a processor of a computer or other programmable data processing device generate a device for implementing the functions specified in one or more flow charts and or one or more block charts.

These computer program instructions can also be stored in a computer-readable memory capable of guiding a computer or other programmable data processing devices to work in a specific way, such that the instructions stored in this computer-readable memory produce a manufacturing including an instruction device that implements functions specified in a flow chart one process or more processes and/or box plot one box or more boxes.

These computer program instructions can also be loaded onto a computer or other programmable data processing device such that a series of operational steps are performed on the computer or other programmable device to produce computer implemented processing, whereby instructions performed on the computer or other programmable device provide the steps used to implement the functions specified in a flow chart one process or more processes and/or box figure one box or more boxes.

In a typical configuration, computing devices include one or more processors (CPUs), input/output interfaces, network interfaces, and memory.

Memory may include such forms as non-permanent memory, random access memory (RAM) and/or non-volatile memory in computer readable media as read-only memory (ROM) or flash memory (flash RAM). Memory is an example of a computer readable medium.

Computer readable media including permanent and non-permanent, movable and non-movable media can be produced by any method or technology to achieve information storage. Information can be computer-readable instructions, data structures, modules of programs, or other data. Examples of the storage media of computers include, but are not limited to, phase-range access memory (PRAM), static random access memory (SRAM), dynamic random access memory (DRAM), other types of random access memory (RAM), read-only memory (ROM), electrically removable programmable read-only memory (EEPROM), flash memory or other memory technologies, read-only optical disc read-only memory (CD-ROM), digital multi-purpose discs (DVD) or other optical storage, magnetic cassettes, Tape magnetic disk storage or other magnetic storage is designed to store information that can be accessed by computing devices. As defined in this article, computational or any other nontransmission media, computer-readable media does not include transitory media, such as modulated data signals and carriers.

It is also necessary to state that the terms "include", "contain", or any other variant thereof is meant to encompass non-exclusive inclusion, such that a process, method, commodity or device comprising a range of elements, not only those elements, but also packages include other elements that are not explicitly listed or are elements that are also inherent to such a process, method, commodity, or device. In the absence of more restrictions, the elements, bounded by the statement "include a . . . ", are not excluded from including the stated. Additional, identical elements exist in the process, method, commodity, or equipment of a voxel.

One skilled in the field should understand that the embodiments of the present application can be provided as methods, systems, or computer program products. Therefore, the application may employ a complete hardware embodiment, a complete software embodiment or an embodiment incorporating aspects of both software and hardware forms. Moreover, the application may take the form of a computer program product implemented on one or more computer available storage media (including, but not limited to, disk memory, CD-ROM, optical memory, etc.) which contain computer available program codes.

The above description is only an embodiment of the application and is not intended to limit the application. For those skilled in the field, the application may have various changes and variations. Any modification, equivalent replacement, improvement, etc. made within the spirit and principle of this application shall be included in the scope of claims of this application.

What is claimed is:

1. A stenosis assessment method based on intracranial DSA imaging, comprising the following steps:
   acquire intracranial DSA(Digital Subtraction Angiography) imaging and extract two planar images containing a target vessel from the DSA imaging, wherein the two planar images have different shooting angles;
based on the two planar images, build a 3D model of the target vessel;
based on the 3D model of the target vessel and the DSA imaging, perform a hemodynamic simulation of the target vessel to derive specified stenosis assessment parameters, including:
from the DSA imaging, determine the start and end frame of the contrast agent flow through the target vessel; and determine a mean blood flow velocity according to the following formula:

$$V=L/((F2-F1)/fps);$$

where, V is the mean blood flow velocity, L is the target vessel length, fps is the frame rate of the DSA imaging, F1 is the frame number of the starting frame, F2 is the frame number of the ending frame;
determine F1 by the following steps:
calculate a first average gray scale frame by frame, which is the average of pixel value over an area of n*n range with a starting point of the target vessel as center point in the DSA imaging;
the first average gray scale of each frame is subtracted from the first average gray scale of a first frame to obtain the corresponding contrast agent concentration of each frame;
arrange the corresponding contrast agent concentration of each frame in time order to obtain the contrast agent time-concentration curve at the starting point;
search for the maximum point Imax of the curve, and set the contrast agent inflow mark threshold a based on the maximum point;
search for the first point greater than or equal to σ on the curve, taking the image frame number corresponding to that point as F1; and
F2 is determined by the same steps as F1, in which the starting point of the target vessel is replaced by an ending point of the target vessel.

2. The method according to claim 1, further including:
acquire intracranial DSA imaging taken at different angles in two groups;
search for a key frame whose second average gray scale is the lowest in every group;
extract an enhanced features of two key frames to obtain a skeleton of vascular tree; and
determine the starting point and ending point of the target vessel, cut the target vessel from the vascular tree skeleton diagram to obtain two planar images containing the target vessel.

3. The method according to claim 2, further including:
after importing the DSA imaging, calculate the second average gray scale frame by frame; and
the image size is M*N and the total number of frames of the imaging is K, the second average gray scale calculation formula is:

$$I_k = E_{i=1}^{M} \Sigma_{j=1}^{N} I(ij)/(M*N),$$

where $I_k$ is the k-th frame second average gray scale and I(i, j) is the gray scale at image coordinate (i, j); the key frame O is defined as O=arg min($I_k$), wherein the operator arg min represents the value of the argument when the minimum value of $I_k$ is reached.

4. The method according to claim 2, further including:
the two key frames are successively processed by Gaussian smoothing, resampling, Hessian matrix enhancement, binarization, and corrosion algorithm thinning to obtain the skeleton of the vascular tree.

5. The method according to claim 1, further including:
extract the center line and boundary lines of the target vessel in each planar image;
determine a matching relationship of the center lines of the target vessel in two planar images, and determine the 3D center line of the target vessel in 3D space according to the matching relationship; and
determine the 3D model of the target vessel according to the 3D center line of the target vessel and the matching relationship.

6. The method according to claim 1, further including:
for a planar image, determine the starting point and ending point of the target vessel;
determine the center line between the starting point and the ending point-by a minimum path algorithm;
determine multiple sample points on the center line;
based on the multiple sampling points the planar image is resampled along the normal direction of the center line to obtain a resampled image;
in the resampled image, determine the boundary intensity value of each sampling point to obtain a boundary intensity image; and
in the boundary intensity image, determine two boundary lines corresponding to the center line by the minimum path algorithm.

7. The method according to claim 1, wherein based on the 3D model of the target vessel and the DSA imaging, perform the hemodynamic simulation of the target vessel to derive specified the stenosis assessment parameters, further comprising:
discretize the 3D model of the target vessel into multiple 3D center points; and
determine the length from each 3D center point to the starting point, as well as the corresponding cross-section area of each center point; and determine a mean blood flow according to the following formula:

$$Q = V * \int_{i=1}^{N1} S_i / N1$$

where, V is the mean blood flow velocity within the target vessel and $S_i$ is the vessel cross-sectional area corresponding to the i-th 3D center point, N1 is the amount of 3D center points.

8. The method of claim 7, wherein based on the 3D model of the target vessel and the DSA imaging, perform the hemodynamic simulation of the target vessel to derive specified the stenosis assessment parameters, further comprising:
for a 3D center point, determine the pressure drop of the 3D center point relative to the starting point according to the following formula:

$$DP_i = a*V + b*V^2 + c*V,$$

where, $DP_i$ is the pressure drop at the i-th 3D center point relative to the origin of the target vessel, a is the viscous loss coefficient, b is the distension loss coefficient, and c is the Bernoulli coefficient; and
the determined pressure drop of each 3D center point forms a blood pressure gradient, PG.

9. The method of claim 8, wherein based on the 3D model of the target vessel and the DSA imaging, perform the hemodynamic simulation of the target vessel to derive specified the stenosis assessment parameters, further comprising:

determine a blood pressure ratio according to the following formula:

$$PR = 1 - PG/Pa;$$

where, PR is the blood pressure ratio, PG is the blood pressure gradient, and Pa is a proximal pressure of the lesion.

10. A device for evaluating the blood flow state of intracranial blood vessels, comprising:

image processing unit is configured to acquire intracranial DSA(Digital Subtraction Angiography) imaging and extract two planar images of the key frames of a target vessel from the DSA imaging with different shooting angles;

model building unit is configured to build a 3D model of the target vessel from the two planar images described;

the numerical simulation unit is configured to simulate the hemodynamics of the target vessel based on the 3D model to derive specified stenosis assessment parameters, including:

determine the start frame and end frame of the contrast agent flowing through the target vessel according to the DSA imaging; and determine a mean blood flow velocity is determined according to the following formula:

$$V = L/((F2-F1)/fps);$$

where, V is the mean blood flow velocity, L is the target vessel length, fps is the frame rate of the DSA imaging, F1 is the frame number of the starting frame, F2 is the frame number of the ending frame;

determine F1 by the following steps:

calculate a first average gray scale frame by frame, which is the average of pixel value over an area of n*n range with a starting point of the target vessel as center point in the DSA imaging;

the first average gray scale of each frame is subtracted from the first average gray scale of a first frame to obtain the corresponding contrast agent concentration of each frame;

arrange the corresponding contrast agent concentration of each frame in time order to obtain the contrast agent time-concentration curve at the starting point;

search for the maximum point Imax of the curve, and set the contrast agent inflow mark threshold σ based on the maximum point;

search for the first point greater than or equal to σ on the curve, taking the image frame number corresponding to that point as F1; and F2 is determined by the same steps as F1, in which the starting point of the target vessel is replaced by an ending point of the target vessel.

* * * * *